(12) United States Patent
Schwertfeger et al.

(10) Patent No.: US 6,365,638 B1
(45) Date of Patent: *Apr. 2, 2002

(54) PROCESS FOR PREPARATION OF HYDROPHILIC OR PARTIALLY HYDROPHILIC INORGANIC AEROGELS

(75) Inventors: Fritz Schwertfeger, Frankfurt; Andreas Zimmermann, Griesheim, both of (DE)

(73) Assignee: Hoechst Aktiengesellschaft, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,478

(22) PCT Filed: Feb. 22, 1996

(86) PCT No.: PCT/EP96/00741

§ 371 Date: Aug. 20, 1997

§ 102(e) Date: Aug. 20, 1997

(87) PCT Pub. No.: WO96/26890

PCT Pub. Date: Sep. 6, 1996

(30) Foreign Application Priority Data

Feb. 22, 1995 (DE) .......................... 195 06 141

(51) Int. Cl.[7] .............................. B01J 13/00; E04B 1/76
(52) U.S. Cl. .................... 516/100; 516/98; 516/111; 516/112; 252/62; 501/12; 423/338; 502/233; 427/220
(58) Field of Search .................. 252/315.2, 315.6, 252/62; 501/12; 423/338; 516/98, 100, 111, 112; 502/233; 427/219, 220

(56) References Cited

U.S. PATENT DOCUMENTS

| 4,327,065 A | | 4/1982 | von Dardel et al. ........ 423/338 |
|---|---|---|---|
| 4,667,417 A | * | 5/1987 | Graser et al. ............ 252/315.6 |
| 4,954,327 A | * | 9/1990 | Blount ........................ 423/338 |
| 4,971,779 A | * | 11/1990 | Paine, Jr. et al. ............. 501/12 |
| 5,122,291 A | * | 6/1992 | Wolff et al. ............... 252/315.6 |
| 5,141,806 A | * | 8/1992 | Koontz .................... 428/315.5 |
| 5,270,027 A | | 12/1993 | Balducci et al. ............ 423/338 |
| 5,275,796 A | | 1/1994 | Tillotson et al. ............ 423/338 |
| 5,565,142 A | * | 10/1996 | Deshpande et al. ...... 252/315.2 |
| 5,587,107 A | * | 12/1996 | Schwertfeger et al. ........ 252/62 |
| 5,647,962 A | * | 7/1997 | Jansen et al. ............... 502/233 |
| 5,705,535 A | * | 1/1998 | Jansen et al. ............... 423/338 |
| 5,759,506 A | * | 6/1998 | Jansen et al. ............... 502/233 |
| 5,789,075 A | * | 8/1998 | Frank et al. .................. 501/12 |
| 5,795,556 A | * | 8/1998 | Jansen et al. ............... 423/338 |
| 5,811,031 A | * | 9/1998 | Jansen et al. ............... 423/338 |

FOREIGN PATENT DOCUMENTS

| DE | 43 00 598 A1 | * | 7/1994 |
| EP | 0018955 | | 11/1980 |
| EP | 0537851 | | 4/1993 |
| EP | 0658513 | | 6/1995 |
| WO | WO 92/03378 | | 3/1992 |
| WO | WO 95/06617 | | 3/1995 |

OTHER PUBLICATIONS

Hawley's Condensed Chemical Dictionary, Eleventh Edition, Edited by sax and Lewis, Sr. (Van Nostrand Reinhold Co., NY, NY, copyright 1987) pp. 985, Oct. 1989.*

G. Poelz et al., Nuclear Intruments and Methods, 195, No. 3, (1982) pp. 491–503, 1982.*

* cited by examiner

Primary Examiner—Daniel S. Metzmaier
(74) Attorney, Agent, or Firm—Frommer Lawrence & Haug LLP

(57) ABSTRACT

Process for preparation of hydrophilic or partially hydrophilic inorganic aerogels. The invention relates to a process for the preparation of hydrophilic or partially hydrophilic inorganic aerogels, which comprises pyrolyzing a hydrophobic inorganic aerogel in the presence of oxygen at temperatures in the range from 100 to 1000° C.

7 Claims, No Drawings

PROCESS FOR PREPARATION OF HYDROPHILIC OR PARTIALLY HYDROPHILIC INORGANIC AEROGELS

CROSS REFERENCE TO RELATED APPLICATIONS

This application is filed under 35 C.F.R. 371 based on PCT/EP96/00741, filed Feb. 22, 1996.

BACKGROUND OF THE INVENTION

The invention relates to a process for preparation of hydrophilic or partially hydrophilic inorganic aerogels from hydrophobic inorganic aerogels.

1. Field of the Invention

Aerogels, in particular those with porosities of greater than 60% and densities of less than 0.6 g/cm$^3$, have extremely low thermal conductivity and are therefore used as thermal insulation material, for example as described in EP-A-0 171 722.

2. Description of the Related Art

Aerogels in the wider sense, ie. in the sense of "gel with air as dispersion medium" are prepared by drying a suitable gel. The term "aerogel" in this sense is taken to mean aerogels in the narrower sense, xerogels and cryogels, a dried gel being termed an aerogel in the narrower sense if the gel liquid is removed to a very large extent at temperatures above the critical temperature and starting at pressures above the critical pressure. If, in contrast, the gel liquid is removed subcritically, for example with formation of a liquid-vapor boundary phase, then the resultant gel is termed a xerogel.

In the present application, the term aerogel is taken to mean aerogels in the wider sense, ie. in the sense of "gel with air as dispersion medium".

This term is taken to exclude xerogels known from the earlier literature, for example those obtained by precipitation of silica (eg. DE-A-30 25 437 and DD-A296 898), or produced in the form of pyrogenic silica (eg. Aerosil®). In these cases, however, the preparation does not give a homogeneous three-dimensional gel structure which extends across relatively large distances.

Aerogels may fundamentally be divided into inorganic and organic aerogels.

Inorganic aerogels were known as early as 1931 (S. S. Kistler, Nature 1931, 127, 741). Since then, aerogels have been prepared from a wide variety of starting materials. For example, $SiO_2$ aerogels, $Al_2O_3$ aerogels, $TiO_2$ aerogels, $ZrO_2$ aerogels, $SnO_2$ aerogels, $Li_2O$ aerogels, $CeO_2$ aerogels, $V_2O_5$ aerogels and mixtures of these have been prepared (H. D. Gesser, P. C. Goswami, Chem. Rev. 1989, 89, 765ff). Organic aerogels made from a wide variety of starting materials, for example from melamine formaldehyde, have also been known for some years (R. W. Pekala, J. Mater. Sci. 1989, 24, 3221).

Inorganic aerogels can be prepared by two fundamentally different methods.

Firstly, $SiO_2$ aerogels, for example, can be prepared by acid hydrolysis and condensation of tetraethyl orthosilicate in ethanol. This gives a gel which can be dried supercritically with retention of the structure. Preparation processes based on this drying technique are known, for example, from EP-A-0 396 076, WO 92/03378 and WO 95/06617.

A fundamental alternative to supercritical drying is provided by a process for subcritical drying of $SiO_2$ gels, in which the $SiO_2$ gel can be obtained, for example, by acid hydrolysis of tetraalkoxysilanes in a suitable organic solvent, using water. After exchanging the solvent for a suitable organic solvent, the resultant gel is reacted with a silylating agent, in a further step. The $SiO_2$ gel thus obtained can then be dried from an organic solvent in air. Aerogels with densities of less than 0.4 g/cm$^3$ and porosities of greater than 60% can be attained in this way. The preparation process based on this drying technique is described in detail in WO 94/25149.

The gels described above may moreover be mixed with tetraalkoxysilanes and aged before drying in the aqueous alcoholic solution, in order to increase the strength of the gel structure, for example as disclosed in WO 92/20623.

However, the tetraalkoxysilanes used as starting materials in the processes described above are exceptionally costly. A considerable reduction in costs can be achieved by using water glass as starting material for preparing the $SiO_2$ gels, for example starting with an aqueous water glass solution and using an ion-exchange resin to prepare a silica which polycondenses on addition of a base to give an $SiO_2$ gel. After exchanging the aqueous medium for a suitable organic solvent, the resultant gel is then reacted with a chlorine-containing silylating agent, in a further step. The $SiO_2$ gel thus obtained, modified on its surface with, for example, methylsilyl groups, can then likewise be dried in air from an organic solvent. The preparation process based on this technique is known from DE-A-43 42 548. Alternative processes relating to the preparation of an $SiO_2$ hydrogel based on water glass followed by subcritical drying are described in the German Patent Applications 195 41 715.1 and 195 41 992.8.

German Patent Application 195 02 453.2 moreover describes the use of chlorine-free silylating agents in the preparation of subcritically dried aerogels.

German Patent Application 195 34 198.8, furthermore, describes an organofunctionalization using organofunctionalized silylating agents in the preparation of subcritically dried aerogels.

EP-A-0 606 638 discloses, furthermore, the preparation of $SiO_2$ aerogels containing carbon particles by heating organically modified $SiO_2$ aerogels in the presence of at least one pyrolyzable hydrocarbon gas and/or at least one inert gas. The organic groups on the surface of the aerogels and/or those of the hydrocarbon gas are oxidized here in an oxygen-free atmosphere to give elemental carbon.

Depending on the solvent used in the supercritical drying, the aerogels obtained by supercritical drying are hydrophilic because of OH groups on the internal surface (supercritical drying from $CO_2$) or hydrophobic in the short term because of alkoxy groups on the internal surface (supercritical drying from alcohols). However, in the long term a reaction of the alkoxy groups with water from the surroundings takes place and leads to formation of hydroxide groups on the internal surface, again giving a hydrophilic aerogel.

The formation of a hydrophilic aerogel can be avoided by a hydrophobicization step during the supercritical drying. For this, a hydrophobicizing agent, for example $Me_2Si(OMe)_2$, can be used, as disclosed in EP-A-0 396 076, for example. The methylsilyl groups on the internal surface make the resultant aerogels permanently hydrophobic.

As a result of the preparation process (silylation before drying), subcritically dried aerogels are permanently hydrophobic. Since the subcritical drying of aerogels requires unreactive, hydrophobic internal gel surfaces, direct preparation of hydrophilic, subcritically dried aerogels is impossible.

For many applications, however, a hydrophilic or partially hydrophilic internal surface of the aerogels is precisely what is essential or advantageous.

It was therefore an object of the present invention to provide a process for preparation of hydrophilic or partially hydrophilic inorganic aerogels, but without having to accept the disadvantage of supercritical drying, with its disproportionately high technical complexity.

This object is achieved by means of a process in which a hydrophobic inorganic, preferably subcritically dried, aerogel is pyrolyzed in the presence of oxygen at temperatures in the range from 100 to 1000° C.

BRIEF SUMMARY OF THE INVENTION

Not Applicable

DETAILED DESCRIPTION OF THE INVENTION

For the purposes of the present application, the term "the presence of oxygen" is taken to mean that a sufficient amount of oxygen is present to oxidize the surface groups of the aerogels, it being possible for this amount to be present in any formulation known to the person skilled in the art (e.g.: air, oxygen-air mixture and/or oxygen-inert gas mixture).

For the purposes of the present application, the term "inorganic aerogel" is taken to mean an aerogel whose preparation has been based on inorganic materials.

The term "aerogels based on inorganic materials" is taken, in particular, to include those aerogels which have been modified, for example, by silylation.

Preference is given to aerogels having hydrophobic surface groups, said aerogels consisting predominantly of $SiO_2$, $Al_2O_3$, $TiO_2$, $ZrO_2$, or mixtures of these. Such aerogels having hydrophobic surface groups can be prepared by any process known to the person skilled in the art. Particular preference is given to hydrophobic $SiO_2$-containing aerogels, in particular $SiO_2$ aerogels.

In a preferred embodiment, the aerogel is pyrolyzed at temperatures from 100 to 1000° C., particularly preferably at from 150 to 800° C., in particular at from 250 to 650° C., in a gentle flow of air.

The duration of the pyrolysis is essentially determined by the surface modification and the density of the material of the aerogels. The duration of the pyrolysis is preferably less than 10 hours, particularly preferably less than 1 hour.

If partially hydrophilic aerogels are to be prepared, the temperature and the duration of the pyrolysis should be adjusted so that only an appropriate proportion of the organic surface groups pyrolyzes.

If the aerogels have different organic groups on their internal surface, the different decomposition temperature of the individual organic groups can be used to pyrolyze the appropriate groups in a controlled fashion and in accordance with the desired degree of hydrophilicity. In the case of aerogels having both phenyl and methyl groups on their internal surface, for example, properties which are partly hydrophilic can then be achieved by pyrolysis at 450° C., which substitutes hydroxide groups for the methyl groups on the surface of a corresponding aerogel, but not for the phenyl groups which are present.

The novel preparation of the hydrophilic aerogels is described below using working examples, but without being restricted by these.

EXAMPLE 1

1 l of a sodium water glass solution (with a content of 7% by weight of $SiO_2$ and an $Na_2O:SiO_2$ ratio of 1:3.3) was stirred with 0.5 l of an acid ion-exchange resin (stryene-divinylbenzene copolymer having sulfonic acid groups, commercially available under the name ®Duolite C20), until the pH of the aqueous solution was 2.3. The ion-exchange resin was then filtered off, and the aqueous solution was adjusted to pH 4.7, using 1 molar NaOH solution. The resultant gel was then aged for a further 3 hours at 85° C., and the water was then exchanged for acetone, using 3 l of acetone. The acetone-containing gel was then silylated with trimethylchlorosilane (5% by weight of trimethylchlorosilane per gram of wet gel). The gel was dried in air (3 hours at 40° C. then 2 hours at 50° C. and 12 hours at 150° C.).

The resultant transparent aerogel had a density of 0.2 g/cm$^3$; its BET specific surface area was 480 m$^2$/g and it was permanently hydrophobic.

The permanently hydrophobic aerogel thus prepared was pyrolyzed at 600° C. in a gentle flow of air in a tube furnace, for 1 hour. The resultant transparent aerogel had a density of 0.21 g/cm$^3$, a BET specific surface area of 450 m$^2$/g, a thermal conductivity λ of 20 mW/mK, and was hydrophilic.

EXAMPLE 2

1 l of a sodium water glass solution (with a content of 7% by weight of $SiO_2$ and an $Na_2O:SiO_2$ ratio of 1:3.3) was stirred with 0.5 l of an acid ion-exchange resin (stryene-divinylbenzene copolymer having sulfonic acid groups, commercially available under the name ®Duolite C20), until the pH of the aqueous solution was 2.3. The ion-exchange resin was then filtered off, and the aqueous solution was adjusted to pH 4.7, using 1 molar NaOH solution. The resultant gel was then aged for a further 3 hours at 85° C., and the water was then exchanged for acetone, using 3 l of acetone. The acetone-containing gel was then silylated with a mixture of trimethylchlorosilane and diphenylmethylchlorosilane (2% by weight of trimethylchlorosilane per gram of wet gel and 2% by weight of diphenylmethylchlorosilane per gram of wet gel). The gel was dried in air (3 hours at 40° C. then 2 hours at 50° C. and 12 hours at 150° C.).

The resultant transparent aerogel had a density of 0.15 g/cm$^3$; its BET specific surface area was 480 m$^2$/g and it was permanently hydrophobic.

The permanently hydrophobic aerogel thus prepared was pyrolyzed at 450° C. in a gentle flow of air in a tube furnace, for 20 minutes. The resultant transparent aerogel had a density of 0.17 g/cm$^3$, a BET specific surface area of 450 m$^2$/g, a thermal conductivity λ of 22 mW/mK, and was only partially hydrophilic.

The thermal conductivity was measured using a hot wire method (see, for example, O. Nielsson, G. Rüschenpöhler, J. Groβ, J. Fricke, High Temperatures—High Pressures, Vol. 21, 267-274 (1989)).

What is claimed is:

1. A process for preparation of hydrophilic or partially hydrophilic inorganic aerogels which comprises pyrolyzing, in the presence of oxygen and at temperatures in the range from 250 to 1000° C., a hydrophobic inorganic aerogel having hydrophobic surface groups, said aerogel having been modified by silylation wherein the inorganic aerogel is selected from the group consisting of $SiO_2$, $Al_2O_3$, $TiO_2$, $ZrO_2$ or mixtures thereof.

2. The process as claimed in claim 1, wherein said hydrophobic aerogel is a subcritically dried aerogel.

3. The process as claimed in claim 1, wherein said hydrophobic inorganic aerogel is pyrolyzed at a temperature in the range of from 250 to 800° C.

4. The process as claimed in at least one of claim 1, wherein the pyrolysis is carried out in air.

5. The process as claimed in at least one of claim 1, wherein the pyrolysis is carried out in a gentle flow of air.

6. The process as claimed in claim 1 wherein the pyrolysis is carried out in less than 10 hours.

7. The process as claimed in claim 1 wherein the pyrolysis is carried out in less than one hour.

* * * * *